United States Patent [19]

Peterson et al.

[11] Patent Number: 5,169,989

[45] Date of Patent: Dec. 8, 1992

[54] FOAM SLABSTOCK POLYETHER POLYOLS WITH IMPROVED SCORCH CHARACTERISTICS

[75] Inventors: Alfred L. Peterson, Coraopolis, Pa.; Mark S. Solomon, Humble; Kenneth E. Reed, Baytown, both of Tex.; Edward P. Squiller, Pittsburgh, Pa.

[73] Assignee: Miles Inc., Pittsburgh, Pa.

[21] Appl. No.: 662,878

[22] Filed: Mar. 1, 1991

[51] Int. Cl.$^5$ ............................................. C07C 43/11
[52] U.S. Cl. ..................................... 568/621; 568/39; 568/57; 568/62; 568/606; 568/613; 568/618; 568/619; 568/622; 568/623; 564/463; 564/475
[58] Field of Search ............... 568/618, 619, 621, 622, 568/623, 613, 606, 39, 57, 62; 564/463, 475

[56] References Cited

U.S. PATENT DOCUMENTS

| | | | |
|---|---|---|---|
| 3,715,402 | 2/1973 | Louvar et al. | 260/613 B |
| 3,833,669 | 9/1974 | Gehm et al. | 260/615 B |
| 4,029,879 | 6/1977 | Muzzio | 536/4 |
| 4,137,396 | 1/1979 | Louvar et al. | 536/4 |
| 4,306,943 | 12/1981 | Mori | 568/621 |

OTHER PUBLICATIONS

Ullman's Encyclopedia of Industrial Chemistry, vol. 19, pp. 301 et seq.
Ullman's Encyclopedia of Industrial Chemistry, vol. 19, pp. 31 et seq.

*Primary Examiner*—Marianne M. Cintins
*Assistant Examiner*—Michael B. Hydorn
*Attorney, Agent, or Firm*—Joseph C. Gil; Godfried R. Akorli

[57] ABSTRACT

An improved process for preparing a polyether polyol of reduced scorching properties comprising buffering of the alkaline polyether polyol before heating to remove water, and the use of said polyether polyol to prepare flexible foam slabstocks.

10 Claims, No Drawings

FOAM SLABSTOCK POLYETHER POLYOLS WITH IMPROVED SCORCH CHARACTERISTICS

BACKGROUND OF THE INVENTION

1. Field of the Invention

The present invention relates to flexible foam slabstocks and methods of preparing the same. More specifically, the present invention relates to a process for reducing or preventing scorching of flexible foam slabstocks by using certain polyether polyols.

2. A Brief Description of the Prior Art

The use of polyether polyols as reactants with polyisocyanates in the preparation of flexible foam slabstocks is generally known in the art. It has been found that scorching is caused, at least in part, by the use of certain polyether polyols, e.g. acidified polyether polyols. The kind of scorching which is of concern here is the discoloration of foams due to high temperatures caused by the associated exothermic reactions.

Polyether polyols can be prepared by the polyaddition reaction of alkylene oxides and starter compounds having active hydrogen atoms, in the presence of basic catalysts. As is generally known, the resultant alkaline polyether polyols are purified by removing or deactivating the residual basic materials such as alkali metal hydroxides or metal salts which are employed in or result from the preparation of the polyether polyols. Known purification processes involve the use of various mineral or organic acids. It is believed that the manner in which the polyether polyol is treated during the purification process can, at least in part, cause the problem of scorching.

Attempts at solving the scorching problem with polyols neutralized by acidification have been unsuccessful. Varying the levels and types of antioxidants, for example, has been unsuccessful in reducing or preventing scorching of foam slabstock made with these polyols. By the present invention there is provided a process for reducing or preventing the problem of scorching.

SUMMARY OF THE INVENTION

In accordance with the foregoing, the present invention encompasses an improved process for preparing a polyether polyol comprising reacting an alkylene oxide with a starter molecule having active hydrogen containing atoms, in the presence of a base catalyst, the improvement comprising buffering the polyether polyol before heating to remove water from the resultant polyether polyol. Typically, the resultant polyether polyol is subjected to distillation by heating to remove water therefrom. It is a distinct feature of the invention that polyether polyol is buffered before heating to remove water. The polyether polyols prepared by the process are encompassed by the invention.

The invention further encompasses a process for preparing a flexible foam slabstock comprising reacting the polyether polyol of the invention with a polyisocyanate. Foams prepared in accordance with the process of the invention are encompassed hereby.

Foams prepared with the polyether polyols in accordance with this invention exhibit a reduced or substantially less scorching. This and other aspects of the invention are discussed more fully hereunder.

DETAILED DESCRIPTION OF THE INVENTION

It was rather surprising to find that under certain conditions which are more fully defined hereunder, the process for preparing polyether polyols, can result in the prevention or reduction of scorching of foams prepared therewith. Accordingly, the present invention is characterized by the process step of buffering of the polyether polyol before heating during work up to remove by products. Buffering at this stage of the process has been found to produce an effective reduction in scorching. By an effective reduction in scorching is meant that differential coloring of the foam is not readily discernible, upon visualization.

Suitable polyether polyols for use in the process of the invention are prepared by methods that are generally known and subject to teachings of this disclosure. The general method of preparing the polyether polyols is described in Saunders and Frisch, Polyurethanes: Chemistry and Technology, Part 1 (1962), pages 32–40. The preparation of the polyether polyols usually involves the use of basic catalysts such as alkali metal hydroxides, e.g., sodium hydroxide, potassium hydroxide, and the like, alkali metal alkoxides such as sodium methoxide, sodium ethoxide, potassium t-butoxide and the like. In the improved process of this invention, the polyether polyol is buffered before heating to remove water therefrom.

In one embodiment of the invention, the step of buffering can comprise reacting the polyether polyol with a buffering agent which is a weak acid. An illustrative but non-limiting example thereof can be carbon dioxide. Typically carbon dioxide is employed in conjunction with water. The amount of carbon dioxide employed would depend on the amount of basic material present in the reaction medium. More specifically, carbon dioxide is employed in an amount of about 2 to 20 and preferably 5 to 10 percent stoichiometric excess over the amount of the basic material. The amount of water employed would be that which is sufficient to provide effective buffering. More specifically water is employed in an amount of about 2 to 5 and preferably 3 to 4 percent by weight based on the weight of the polyether polyol.

The resultant polyether polyol has a pH of 8 to 10 and preferably 9 to 10. The resultant polyether polyol can the be heated to distill water.

In another embodiment of the invention, the step of buffering can comprise reacting the polyether polyol with an acid such as sulfuric acid, followed by reacting the acidified polyether polyol with a buffering agent such as potassium carbonate. Illustrative but non-limiting examples of other acids useful herein can be inorganic acids such as phosphoric acid, hydrochloric acid, potassium hydrogen phosphate and the like; organic acids such as citric acid, tartaric acid and the like. The resultant polyether polyol typically has a pH of about 6 to 6.5.

Illustrative but non-limiting examples of other buffering agents which are useful herein can be other alkali metal carbonates selected from the group consisting of potassium bicarbonate, sodium carbonate, sodium bicarbonate and a mixture thereof. Potassium carbonate is preferred. Illustratively, the preferred potassium carbonate content is from 0.01 to 0.50 percent by weight and from 0.05 to 0.25 percent by weight based on the weight of the polyether polyol.

Typically, the buffering agent is combined with the polyether polyol by, say blending them. The temperature range over which the buffering agent is combined with the polyether polyol can be from ambient temperature to 120 degrees Centigrade and preferably from about 60 to 100 degrees Centigrade. The resultant polyether polyols typically have a pH of about 8 to 10 and preferably 9 to 10.

In the process for preparing the flexible slabstock, the polyether polyol of the invention is reacted with a polyisocyanate, as follows. Foaming is carried out using normal flexible foam formulations containing polyisocyanates, preferably tolylene diisocyanate containing 80% by weight 2,4-isomer and 20% by weight 2,6-isomer ("TDI 80"). The resultant foams exhibit a reduction or prevention in scorching.

The following materials are suitable starting components for the production of the flexible slabstock polyurethane foams according to the process of this invention:

1. Polyisocyanates, including, for example, tolylene diisocyanate isomers, such as 2,4- and 2,6-tolylene diisocyanate and mixtures of these isomers ("TDI"); hexamethylene diisocyanate; and isophorone diisocyanate. Also suitable are carbodiimide-, urethane-, allophanate-, isocyanurate-, urea-, and biuret-modified polyisocyanates derived from 2,4- and 2,6-tolylene diisocyante, hexamethylene diisocyanate, or isophorone diisocyanate. Mixtures of the above polyisocyanates, including the various isomeric forms thereof, are, of course also suitable.

Preferred polyisocyanates for use in accordance with the invention include tolylene diisocyanate in the form of an 80:20 mixture of the 2,4- and 2,6-isomers ("TDI 80"), tolylene diisocyanate in the form of a 65:35 mixture of the 2,4- and 2,6-isomers ("TDI 65"), and tolylene diisocyante prepolymers.

2. The polyether polyols of this invention which can have a molecular weight of from about 400 to about 10,000. Suitable compounds contain amino groups, thiol groups, or carboxyl groups, and preferably include compounds containing hydroxyl groups (especially 2 to 8 hydroxyl groups), particularly those having a molecular weight in the range from about 100 to about 6000 (preferably in the range from 2000 to 6000). The suitable polyethers can be used with other isocyanate reaction resins such as other polyethers, polyesters, polycarbonates, and polyester amides containing at least 2, generally 2 to 8, but preferably 2 to 6, hydroxyl groups, of the type known for the production of homogeneous and cellular polyurethanes and described, for example, in German Offenlegungsschrift 2,832,253, pages 11 to 18. Preferred compounds have an OH value of about 28 to about 56.

3. Optionally, compounds containing at least two isocyanate-reactive hydrogen atoms and having a molecular weight of about 32 to about 399. Suitable compounds contain hydroxyl groups, amino groups, thiol groups, or carboxyl groups, preferably hydroxyl groups and/or amino groups, which serve as crosslinking agents or chain extending agents. These compounds generally contain about 2 to about 8 (preferably 2 to 4) isocyanate-reactive hydrogen atoms. Examples of such compounds can be found in German Offenlegungsschrift 2,832,253, pages 10 to 20.

4. Water as a chemical and physical blowing agent in a quantity of 5 to 15 parts by weight to 100 parts by weight of component (b).

5. Optionally, auxiliaries and additives, such as
   (a) readily volatile organic substances as further blowing agents,
   (b) known reaction accelerators and reaction retarders in the usual quantities,
   (c) surface-active additives, such as emulsifiers and foam stabilizers; known cell regulators, such as paraffins, fatty alcohols, and dimethyl polysiloxanes; pigments or dyes; known flameproofing agents, such as trichloroethyl phosphate and tricresyl phosphate; stabilizers against the effects of aging and weather; plasticizers; fungistatic and bacteriostatic agents; and fillers, such as barium sulfate, kieselguhr, carbon black, and whiting.

These optional auxiliaries and additives are described, for example, in German Offenlegungsschrift 2,732,292, pages 21 to 24. Further examples of surface-active additives and foam stabilizers, cell regulators, reaction retarders, stabilizers, flameproofing agents, plasticizers, dyes and fillers, fungistatic and bacteriostatic agents which may optionally be used in accordance with the invention and information on the use and mode of action of these additives can be found in Kunststoff-Handbuch, Vol. VII, published by Vieweg and Höchtlen, Carl-Hanser-Verlag, Munich, 1966, for example on pages 103 to 113.

The process according to the invention is carried out using the known one-shot process, the prepolymer process, or the semiprepolymer process, often using machines such as those described in U.S. Pat. No. 2,764,565. Information on processing machines which may also be used in accordance with the invention can be found in Kunststoff-Handbuch, Vol. VII, published by Vieweg and Höchtlen, Carl-Hanser-Verlag, Munich 1966, for example, on pages 121 to 205.

The foams produced in accordance with the invention can be used, for example, in the manufacture of seating. Such foams are also used, for example, as fillings in cushions and quilts.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Centigrade and all percentages are percentages by weight.

EXAMPLES

EXAMPLE 1

This example also illustrates the preparation of the polyether polyols of the present invention.

3466 grams of an alkaline polyether polyol (0.5% potassium hydroxide) and 139 grams of water were charged into a 5 liter flask equipped with a mechanical stirrer, thermometer an inlet tube through which gaseous carbon dioxide is bubbled, and a tube connected to a bubbler. The resulting reaction mixture was heated to and maintained at 90 degrees Centigrade for 1 hour. Gaseous carbon dioxide was bubbled into the reaction mixture until a pH of 8–10 was attained. Water was removed by vacuum distillation; the mixture was then filtered and retained for subsequent use.

EXAMPLE 2

This example further illustrates the preparation of the polyether polyols of the present invention.

3508 grams of an alkaline polyether polyol (0.5% potassium hydroxide) was charged into a 5 liter flask equipped with a mechanical stirrer and a thermometer. The polyether polyol was heated to, and maintained at 90 degrees Centigrade for 1 hour, and then neutralized with aqueous sulfuric acid to a pH of 6.5. Potassium carbonate (8.8 grams, 0.25%) was then added and the resultant mixture was held at 90 degrees Centigrade for 30 minutes with stirring. The resultant polyether polyol had a pH of 8 to 10. Water was removed by vacuum distillation. The polyether polyol was then filtered and subsequently used.

EXAMPLE 3

This example illustrates preparation of flexible foam slabstock with a polyether polyol which is prepared using a buffering agent in accordance with the present invention. The following were used in the preparation.

| Ingredients | Parts by Weight(grams) |
| --- | --- |
| Polyether polyol | 100 |
| Water | 5.3 |
| "L-6202" Surfactant (1) | 1.2 |
| "Dabco 33LV" Amine catalyst (2) | 0.1 |
| "T-9" Tin catalyst (3) | 0.22 |
| Methylene chloride | 6.5 |
| "Mondur TD 80" (112 NCO index) (4) | 67.5 |

(1) Available from Union Carbide Co.
(2) Available from Air Products Co
(3) Available from Air Products Co.
(4) Available from Mobay Corp.

The above ingredients were reacted as follows. The polyether polyol, water, surfactant and amine catalyst were blended and mixed thoroughly. The diisocyanate was added and mixed for about seven seconds. Thereafter, the reaction mixture was poured into a 10×10×5 inches box. When the foam had fully risen, it was removed from the box and subjected to a Microwave Scorch Test as described by D. R. Post in the Testing Procedures for Evaluating Antioxidant Efficiency, 32nd Annual Polyurethane Technical/Marketing Conference, Oct. 1–4, 1989.

After the microwave test, the foam was cut and evaluated for scorching.

EXAMPLE 4

This example illustrates preparation of flexible foam slabstock with a polyether polyol which was prepared in essentially the same manner as described in Example 1. The following were used in the preparation.

| Ingredients | Parts by Weight(grams) |
| --- | --- |
| Polyether polyol | 100 |
| Water | 5.3 |
| L-6202 Surfactant | 1.2 |
| T-9 Tin catalyst | 0.1 |
| Methylene chloride | 6.5 |
| TD 80 (112 NCO index) | 67.5 |

The above ingredients were reacted and evaluated in essentially the same manner as described in Example 3.

EXAMPLE 5

Foams prepared in accordance with this invention and those prepared by comparative processes, using the various polyether polyol samples were evaluated for scorching with the results reported in the Table below. The term "neutralization method" was used broadly to denote the step of treating the alkalinepolyether polyols to deactivate the basic materials. In the comparative processes, "Britesorb" absorbent (available from Philadelphia Quartz) was employed by itself and in combination with sulfuric acid (control), as the neutralizing agent. Lactic acid was also used as the neutralizing agent.

The methods of preparing the foams were essentially the same as described in Example 3 with the following exceptions. In some instances as reported in the Table, standard antioxidant packages of 0.20% 2,6-di-tertiary butyl-4-methyl phenol (BHT) and 0.25% "Naugard 445" (available from Uniroyal Co.) were added to the polyether polyol before water was removed. Upon visual inspection, the foams were rated on the scale of 1 to 10 with the least scorched rated as 1.

TABLE

| Polyether Polyol Samples | Neutralization Method | MICROWAVE TESTS BHT*** | Rise Time Average Sec. | Rating Sample 1 | Sample 2 | Sample 3 | Sample Average |
| --- | --- | --- | --- | --- | --- | --- | --- |
| Control | H$_2$SO$_4$-Britesorb | 0.06% | 119 | 5 | 6 | 2 | 4.3 |
| Voranol 3010* | Unknown | Unknown | 119 | 2 | 2 | 1 | 1.6 |
| A | H$_2$SO$_4$-Britesorb 25% | — | | Would not process into a foam | | | |
| B | H$_2$SO$_4$-Britesorb 25% | 0.06% | 122 | 1 | 2 | 6 | 3 |
| C | H$_2$SO$_4$ | — | | Would not process into a foam | | | |
| D | H$_2$SO$_4$ | 0.06% | 140 | 3 | 5 | 3 | 3.6 |
| E | 100% Britesorb | — | 169 | 1 | 1 | 2 | 1.3 |
| F | 100% Britesorb | 0.06% | 113 | 1 | 2 | 1 | 1.3 |
| G | CO$_2$ | — | 152 | 3 | 1 | 3 | 2.3 |
| H | CO$_2$ | 0.06% | 106 | 1 | 1 | 1 | 1 |
| I | 50% H$_2$SO$_4$ 50% Britesorb | — | 115 | 1 | 2 | 2 | 1.6 |
| J | 50% H$_2$SO$_4$ 50% Britesorb | 0.06% | 110 | 3 | 1 | 2 | 2 |
| K | H$_2$SO$_4$ Neut/K$_2$CO$_3$ Buffer | — | 163 | 4 | 2 | 2 | 2.7 |
| L | H$_2$SO$_4$ Neut/K$_2$CO$_3$ Buffer | 0.06% | 122 | 1 | 1 | 1 | 1 |
| M | Lactic Acid (85%) | — | 143 | 3 | 5 | 5 | 4.3 |
| N | Lactic Acid (85%) | 0.06% | 118 | 3 | 3 | 5 | 3.7 |
| O** | Unit Neutralized | — | 120 | 2 | 4 | 2 | 2.7 |
| Control | Repeat | 0.06% | 120 | 1 | 2 | 3 | 2 |
| Voranol 3010 | Repeat | Unknown | 107 | 1 | 1 | 1 | 1 |
| B | Repeat | 0.06% | 110 | 4 | 3 | 2 | 3 |

TABLE-continued

MICROWAVE TESTS

| Polyether Polyol Samples | Neutralization Method | BHT*** | Rise Time Average Sec. | Rating Sample 1 | Sample 2 | Sample 3 | Sample Average |
|---|---|---|---|---|---|---|---|
| Control | Previous 4 Runs Ave. | 0.06% | 111 | | | | 4.5 |

*A polyether polyol available from Dow Chemical Co.
**A polyether polyol which was essentially the same as the control except that it was neutralized during commercial production.
***BHT was added before the removal of water.

As would be seen from the Table above, Samples A and C where no BHT was added before water removal did not process. Samples E, G, K, and M which also had no BHT added before the removal of water had very slow rise and set periods and produced lower block heights. The two samples that showed no scorch were samples H which was buffered with carbon dioxide and sample L which was reacted with sulfuric acid and buffered with potassium carbonate in accordance with this invention. Sample F to which was added 100% "Britesorb" was almost as good as samples H and L. At the level of 100% "Britesorb", the polyether polyol would be rather expensive.

What is claimed is:

1. In an improved process for preparing a polyether polyol comprising reacting an alkylene oxide with a starter molecule having active hydrogen containing atoms, in the presence of a base catalyst and heating the resultant polyether to remove water, the improvement consisting essentially of buffering the polyether polyol after the preparation of and before heating the polyether polyol to remove water from the polyether polyol.

2. The process of claim 1 wherein the step of buffering comprises reacting the polyether polyol with a buffering agent which is a weak acid.

3. The process of claim 2 wherein the step of buffering comprises reacting the polyether polyol with carbon dioxide.

4. The process of claim 1 wherein the step of buffering comprises reacting the polyether polyol with an acid, followed by reacting the acidified polyether polyol with a buffering agent.

5. The process of claim 4 wherein the buffering agent is selected from the group consisting of potassium carbonate, potassium bicarbonate, sodium carbonate, sodium bicarbonate and a mixture thereof.

6. The process of claim 5 wherein the buffering agent is potassium carbonate.

7. The process of claim 6 wherein the potassium carbonate content is from 0.01 to 0.50 percent by weight based on the weight of polyether polyol.

8. The process of claim 7 wherein the potassium carbonate content is from 0.01 to 0.25 percent by weight based on the weight of polyether polyol.

9. The process of claim 1 wherein an antioxidant is added to the polyether polyol before heating to remove water.

10. A polyether polyol with reduced scorching characteristics for use in the preparation of a flexible foam slabstock which is prepared by the process of claim 1.

* * * * *